(12) United States Patent
Takahashi (10) Patent No.: US 7,636,476 B2
(45) Date of Patent: Dec. 22, 2009

(54) RADIATION AREA EXTRACTING METHOD AND IMAGE PROCESSING APPARATUS

(75) Inventor: Naoto Takahashi, Kunitachi (JP)

(73) Assignee: Canon Kabushiki Kaisha, Tokyo (JP)

( * ) Notice: Subject to any disclaimer, the term of this patent is extended or adjusted under 35 U.S.C. 154(b) by 701 days.

(21) Appl. No.: 11/433,138

(22) Filed: May 11, 2006

(65) Prior Publication Data

US 2006/0269141 A1 Nov. 30, 2006

(30) Foreign Application Priority Data

May 31, 2005 (JP) ............................. 2005-159111

(51) Int. Cl.
G06K 9/48 (2006.01)
G06K 9/00 (2006.01)
(52) U.S. Cl. ..................... 382/199; 382/132
(58) Field of Classification Search ................ 382/128, 382/132, 190, 199, 224, 284
See application file for complete search history.

(56) References Cited

U.S. PATENT DOCUMENTS

| 4,967,079 | A | | 10/1990 | Shimura | |
|---|---|---|---|---|---|
| 4,992,663 | A | * | 2/1991 | Takeo | 250/587 |
| 5,732,149 | A | * | 3/1998 | Kido et al. | 382/128 |
| 6,356,651 | B2 | * | 3/2002 | Murakami | 382/128 |
| 6,885,770 | B2 | | 4/2005 | Matsuura | |
| 7,123,761 | B2 | * | 10/2006 | Kawano | 382/132 |
| 2001/0043732 | A1 | | 11/2001 | Matsuura | |
| 2002/0154800 | A1 | | 10/2002 | Shinbata | |

FOREIGN PATENT DOCUMENTS

| JP | 63-259538 A | 10/1988 |
|---|---|---|
| JP | H10-137230 A | 5/1998 |
| JP | 2000-023952 A | 1/2000 |
| JP | 2001-307064 A | 11/2001 |
| WO | 02/099738 A1 | 12/2002 |

* cited by examiner

*Primary Examiner*—Daniel G Mariam
(74) *Attorney, Agent, or Firm*—Canon USA Inc IP Division (57) ABSTRACT

A radiation area extracting method for extracting a radiation area from image data includes generating combinations of at least two candidate lines from an area of the image data, an evaluating step of obtaining evaluated values of the combinations of at least two candidate lines, and an extracting step of extracting one of the combinations of at least two candidate lines as a contour line of the radiation area on the basis of the evaluated values.

10 Claims, 10 Drawing Sheets

| | a b c | SCORE |
|---|---|---|
| PATTERN OF PIXEL VALUE | ascending line | 4 |
| | low-a, high b=c | 3 |
| | peak at b | 2 |
| | a=b, low c | 1 |
| | valley at b | 2 |
| | high a, b=c lower | 1 |
| | descending line | 0 |

RADIATION AREA EXTRACTING METHOD AND IMAGE PROCESSING APPARATUS

BACKGROUND OF THE INVENTION

1. Field of the Invention

The present invention relates to a radiation area extracting method for extracting a radiation area from image data. The present invention also relates to an image processing apparatus such as a radiography apparatus or digital camera.

2. Description of the Related Art

Recently, with the development of digital technology, a technique has been developed for converting radiation to image data as digital image signals, and performing image processing on the image data to display or print the output. In one method, radiation is received through a light receiver (also referred to as a light-receiving surface) and is stored on a stimulable phosphor sheet. Then, the stimulable phosphor sheet is illuminated with excitation light, and photostimulated luminescence from the stimulable phosphor sheet that is caused by this operation is photoelectrically detected to obtain image signals to produce a visible image. In another method, radiation is received through a light receiver that is a two-dimensional sensor and is directly converted to image signals. In yet another method, an analog film that has received radiation through a light receiver included in a cassette case is developed, and the image formed on the developed film is converted to image signals by an analog-to-digital (AD) conversion apparatus.

In radiography, in general, radiation focusing in which only an intended area is illuminated with radiation is performed to prevent radiation from affecting an area other than the intended area and from being scattered from the intended area so as to prevent a decrease in contrast. In this case, a first area that directly receives radiation and a second area that does not receive radiation other than secondary radiation such as scattered radiation are formed on a light receiver by the action of radiation focusing. The first area is referred to as a radiation area. Even when radiation focusing is not performed, radiation may not directly reach the light receiver. Even in this case, the area that directly receives radiation on the light receiver is referred to as a radiation area.

In general, in a case where parameters that are used when gray-level transformation is performed on image data are determined, the image data corresponding to the radiation area is used. Moreover, when image data is printed on a film, a range of the image data to be printed on the film is determined on the basis of the radiation area in some cases.

In this way, various types of processing are performed on the basis of the data of the radiation area in image data.

A method for extracting such a radiation area is disclosed in Japanese Patent No. 2596744. In this method, edge points that are supposed to constitute the edges of a radiation area are extracted in radial directions from the center of a stimulable phosphor sheet to the edges of the sheet. Then, assuming that candidate lines that represent the edges of a radiation area are lines that pass through a predetermined number or more of the extracted edge points, line segments that represent the edges of a final radiation area are extracted by the Hough transformation. Then, an area enclosed with these line segments is regarded as the final radiation area. In this method, the line segments that represent the edges of the final radiation area are not determined on the basis of the relationships between the extracted candidate lines.

Hitherto, line segments that represent the edges of a radiation area have been extracted on the basis of only the information of edge points. In this case, for example, when area segments other than the edges of the radiation area in the image data include straight parts, the radiation area is erroneously extracted in some cases. Thus, various types of solutions have been required.

SUMMARY OF THE INVENTION

In view of the aforementioned problem, the present invention provides a radiation area extracting method and an image capturing apparatus to reduce the frequency with which a radiation area is erroneously extracted.

A radiation area extracting method according to an aspect of the present invention for extracting a radiation area from image data includes generating combinations of at least two candidate lines from an area of the image data, an evaluating step of obtaining evaluated values of the combinations of at least two candidate lines, and an extracting step of extracting one of the combinations of at least two candidate lines as a contour line of the radiation area on the basis of the evaluated values.

Further features of the present invention will become apparent from the following description of exemplary embodiments with reference to the attached drawings.

DESCRIPTION OF THE EMBODIMENTS

Preferred embodiments of the present invention will be described in detail in accordance with the accompanying drawings.

Figure 1:
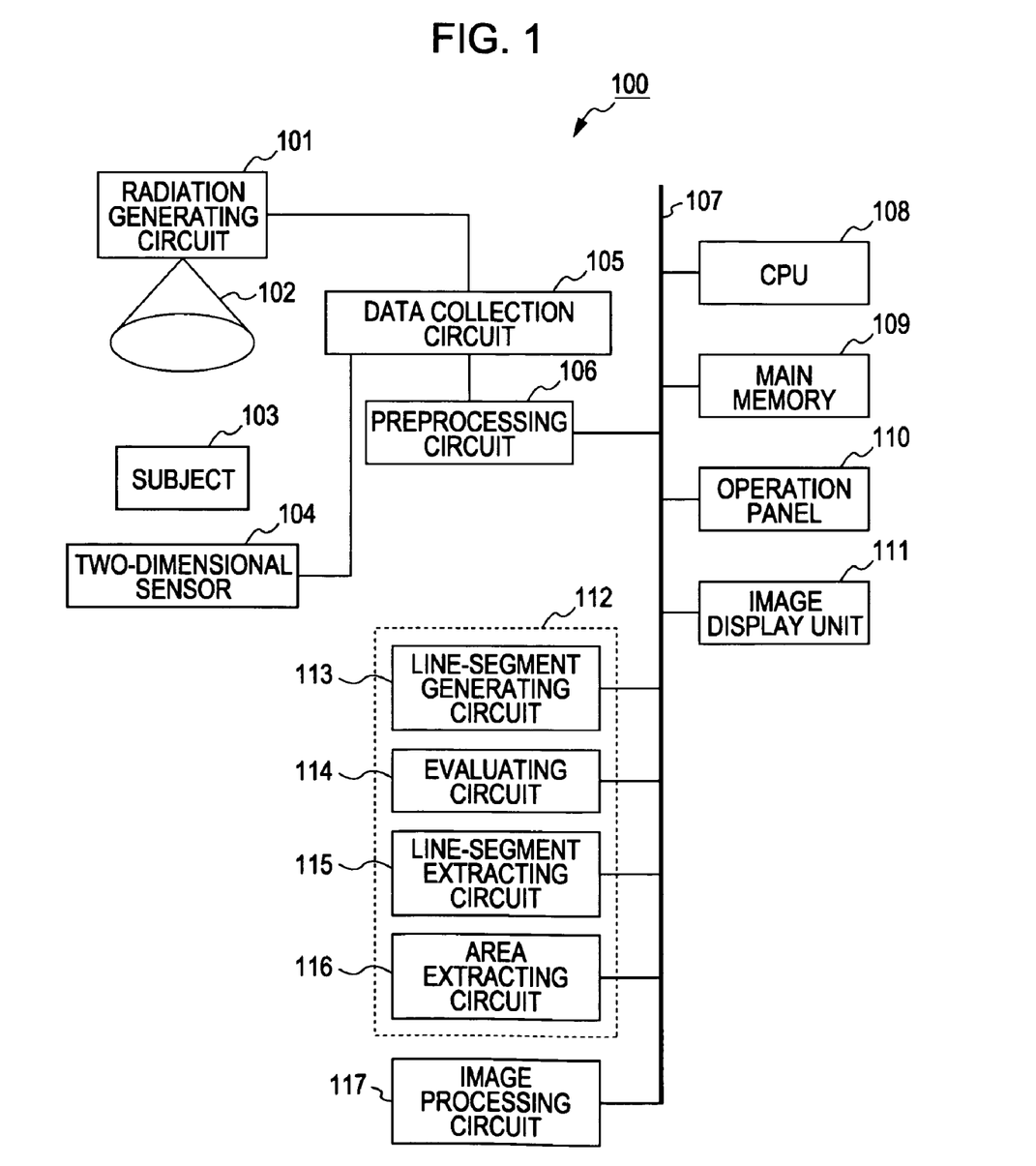
FIG. 1 is a block diagram of an image processing apparatus according to a first exemplary embodiment.

FIG. 1 shows the overall structure of a radiography apparatus that has functions according to the present invention.

Figure 2:
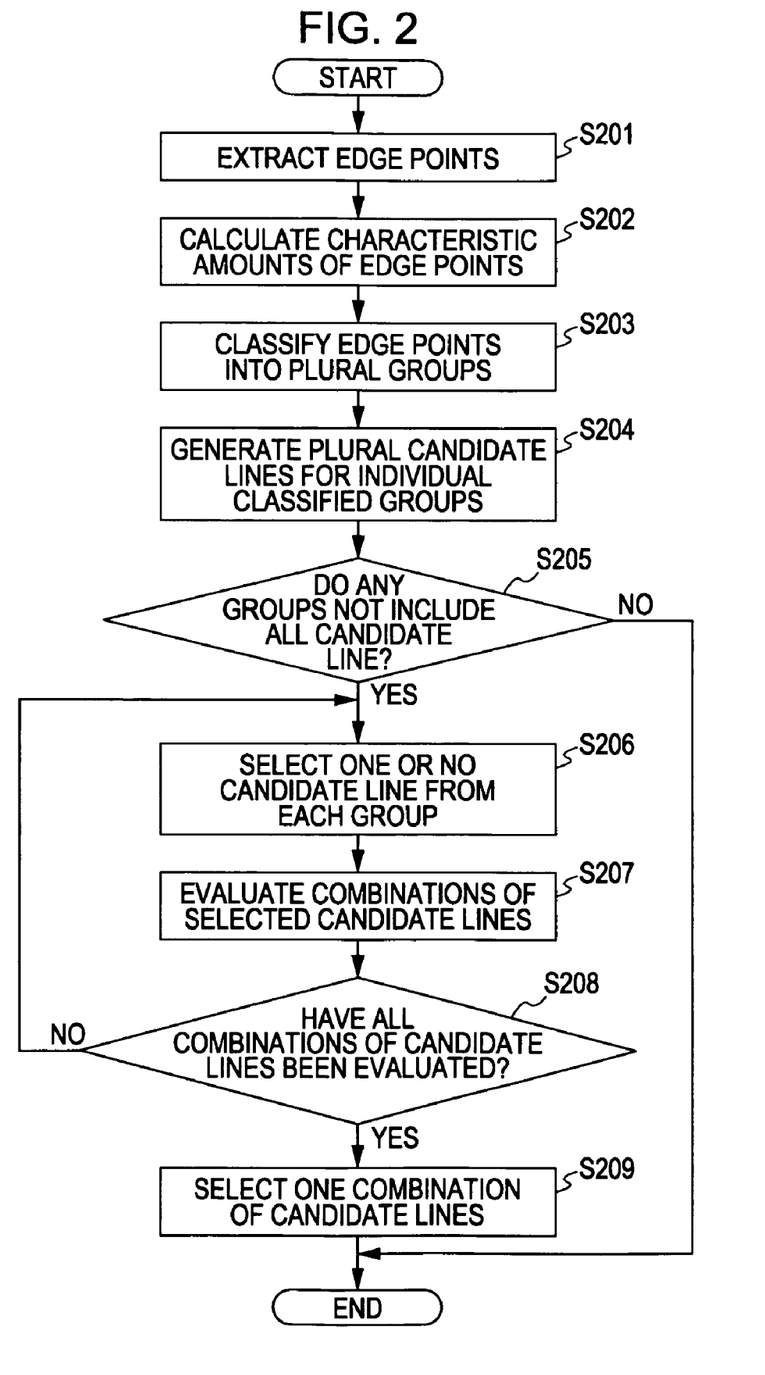
FIG. 2 is a flowchart showing the process flow of a radiation area extracting method according to the first exemplary embodiment.

FIG. 2 is a flowchart showing the process flow of a radiation area extracting method according to a first exemplary embodiment. The first exemplary embodiment will be first described with reference to FIGS. 1 and 2.

The present invention is applied to, for example, a radiography apparatus 100 shown in FIG. 1. The radiography apparatus 100 has a function of outputting image data that is obtained by radiography to a film or a monitor. In general, image processing, such as gray-level transformation and frequency processing, is performed in this process. The radiography apparatus 100 includes a data collection circuit 105, a preprocessing circuit 106, a central processing unit (CPU) 108, a main memory 109, an operation panel 110, an image display unit 111, a radiation area extracting circuit 112, and an image processing circuit 117. These components are connected to each other via a CPU bus 107 so that data can be exchanged among these components.

In the radiography apparatus 100, the data collection circuit 105 and the preprocessing circuit 106 are connected to each other. A two-dimensional radiation sensor 104 and a radiation generating circuit are connected to the data collection circuit 105. The radiation area extracting circuit 112 includes a line-segment generating circuit 113, an evaluating circuit 114, a line-segment extracting circuit 115, and an area extracting circuit 116. The line-segment generating circuit 113 generates a plurality of candidate lines that are assumed to constitute a contour line that represents the outer edges of a radiation area. The evaluating circuit 114 evaluates the combinations of the candidate lines, i.e., the relationships between the candidate lines, on the basis of image data, the combinations being generated by the line-segment generating circuit 113. The line-segment extracting circuit 115 extracts one of the combinations of candidate lines that are evaluated by the evaluating circuit 114 as a combination of line segments that constitute a contour line that represents the edges of a radiation area on the basis of the evaluated values. The area extracting circuit 116 extracts the area enclosed by the line segments that are extracted by the line-segment extracting circuit 115 as a radiation area. These circuits are connected to the CPU bus 107.

The main memory 109 stores programs, various types of data, and the like that are required in the processing that is performed by the CPU 108 and functions as a working memory of the CPU 108. The CPU 108 performs, for example, control of the overall operation of the radiography apparatus 100 using the main memory 109 in response to the operation of the operation panel 110. The radiography apparatus 100 is controlled so as to operate in the following manner. The individual functions of the radiation area extracting circuit 112 can be performed by a computer that operates according to a computer program. In this case, the individual functions of the radiation area extracting circuit 112 are performed by the CPU 108 according to a program stored in the main memory 109.

When a user inputs a shooting instruction through the operation panel 110, the CPU 108 transmits the shooting instruction to the data collection circuit 105. The CPU 108 drives the radiation generating circuit 101 and the two-dimensional radiation sensor 104 upon receiving the shooting instruction to take a radiograph.

When a radiograph is taken, the radiation generating circuit 101 first emits a radiation beam 102 onto a subject 103. The radiation beam 102 emitted from the radiation generating circuit 101 passes through the subject 103, the radiation beam 102 being attenuated, and reaches the light receiver of the two-dimensional radiation sensor 104. Then, the two-dimensional radiation sensor 104 outputs radiographic image signals. The two-dimensional radiation sensor 104 includes a plurality of elements that convert radiation to electrical signals. In this exemplary embodiment, the subject 103 is a human body. That is to say, radiographic image data output from the two-dimensional radiation sensor 104 is image data that is obtained by capturing an image of the human body.

The data collection circuit 105 performs predetermined processing, such as AD conversion, on the image signals output from the two-dimensional radiation sensor 104 to convert the image signals to image data in the form of digital signals. This image data is supplied to the preprocessing circuit 106 and subjected to preprocessing, such as offset correction and gain correction. The image data having been subjected to preprocessing in the preprocessing circuit 106 is transferred as original image data to the main memory 109 and the radiation area extracting circuit 112 via the CPU bus 107 under the control of the CPU 108. In this exemplary embodiment, the radiation area extracting circuit 112 uses data that has been processed by the preprocessing circuit 106. However, the radiation area extracting circuit 112 can perform the same functions as described above on image data that has not been preprocessed.

The radiation area extracting circuit 112 extracts a radiation area from the original image data and generates data of the radiation area. The image processing circuit 117 performs various types of image processing on the original image data on the basis of the data of the radiation area. For example, gray-level correction is performed, in which a histogram of pixel values in a radiation area is obtained on the basis of data of the radiation area and the contrast of an intended area is adjusted to be the contrast that is suitable for diagnostic processing. Moreover, for example, a process of separating only a segment of image data within the radiation area from the image data and transmitting the segment of image data to a printer (not shown) is performed.

The operation of the radiography apparatus 100 having the aforementioned structure according to the first exemplary embodiment will now be described with reference to the flowchart of FIG. 2.

The original image data obtained by the preprocessing circuit 106 is transferred to the radiation area extracting circuit 112 via the CPU bus 107, as described above.

In step S201, the line-segment generating circuit 113 first extracts a plurality of edge points from the image data. In step S202, the characteristic amounts of the edge points are calculated. The edges of a radiation area are boundaries between an area that receives radiation and an area that does not receive radiation on the light receiver. Thus, gradients occur in the pixel values of the edges of the radiation area. Moreover, since radiation is emitted through an emitting aperture having straight sides, the edges of the radiation area tend to be straight. In this description, the emitting aperture has straight sides. However, this exemplary embodiment is applicable even when the emitting aperture has a circular shape. In this exemplary embodiment, the method for extracting edge points is not limited to a specific method, and a derivative operator, such as a known Sobel, Prewitt, or Roberts operator, can be used to calculate values related to gradients as the characteristic amounts of edge points. That is to say, the characteristic amounts of edge points include the coordinates and values related to the gradients of edge points.

Hereinafter, values calculated for individual edge points may be referred to as characteristic amounts. The gradient values of edge points that are supposed to be located on the edges of a radiation area tend to be relatively high compared with those of other components in an image, as described above. Thus, the edge points that have gradient values more than a predetermined threshold value can be extracted as candidate edge points that are supposed to be located on the edges of a radiation area. For example, when an accumulated histogram of the edge gradient values is created and a threshold value is set so that the top 85% or more of the accumulated edge gradient value is covered, a relatively large number of edge points that are located on the edges of a radiation area can be extracted.

In this exemplary embodiment, the Canny method is used as the method for extracting edge points. The Canny method is less likely to be affected by noise and thus is suitable for accurately extracting points that are located on the edges of a radiation area and have a weak edge intensity. Since the Canny method is a well-known method, the details of the Canny method will not be described here. The details of the Canny method are described in, for example, Canny, John.: "A Computational Approach to Edge Detection. IEEE Transaction on Pattern Analysis and Machine Intelligence", Vol. PAMI-8, No. 6, pp. 679-698, 1986. Any method that uses, for example, derivatives or high-order derivatives other than the aforementioned method can be used regarding edge points.

Then, in step S203, the extracted edge points are classified into a plurality of groups. The method for classifying edge points is not limited to a specific method. In this exemplary embodiment, edge points are classified on the basis of the positional relationships between the edge points and the representative point in a radiation area and the gradient directions of the edge points. This method will now be described in detail.

Figure 3:
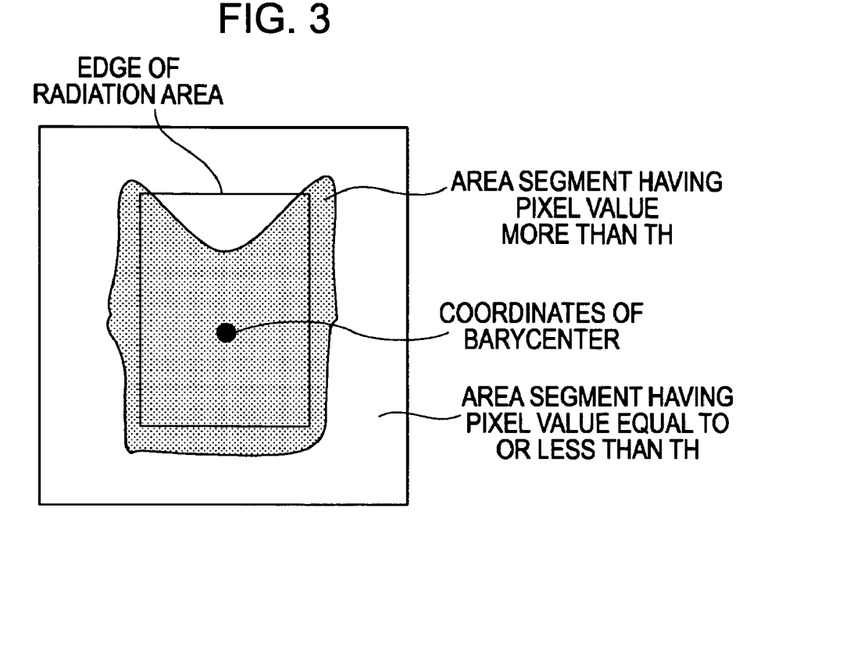
FIG. 3 is used to show a method for calculating coordinates of a barycenter.

FIG. 3 shows a case where the barycenter is used as the representative point in a radiation area. In FIG. 3, the rectangular area, the shaded area, and the point represent a radiation area, an area that has pixel values more than Th, and a barycenter, respectively.

The barycenter $(X_g, Y_g)$ is first extracted as the representative point in the radiation area. Since the area outside the radiation area is shielded from radiation, the pixel values of the area outside the radiation area tend to be small compared with those of the radiation area. Thus, the coordinates of the barycenter of the radiation area are calculated from an image $f(x, y)$ according to the following equation (1) using a predetermined threshold value Th, and the barycenter is set as the representative point in the radiation area.

$$X_g = \sum_y \sum_x x \times \text{sign}(f(x, y)) \bigg/ \sum_y \sum_x \text{sign}(f(x, y)) \quad (1)$$

$$Y_g = \sum_y \sum_x y \times \text{sign}(f(x, y)) \bigg/ \sum_y \sum_x \text{sign}(f(x, y))$$

In equation (1), sign(x) is represented by the following conditional equation (2) with the threshold value Th being the conditional parameter.

sign(x)=1: when x>Th sign(x)=0: when x≦Th    (2)

The higher the pixel values of an area, the higher the probability that the area is located in the radiation area. Thus, the coordinates of a barycenter that is weighted with pixel values may be calculated using the following conditional equation (3) instead of equation (2).

sign(x)=x: when x>Th sign(x)<0: when x≦Th    (2)

The threshold value Th may be empirically determined as a fixed value or a variable value that depends on shooting conditions. Alternatively, for example, the automatic threshold selection method based on criteria can be used. Since the automatic threshold selection method is a well-known method, the details will not be described here. The details of the automatic threshold selection method are described in, for example, N. Otsu,: "A threshold selection method from gray-level histograms, IEEE Trans. on Systems, Man, and Cybernetics", Vol. SMC-9, No. 1, pp. 62-66, 1979.

The threshold value Th is used merely for classifying the pixels according to the pixel values. In an actual image, some area segments outside and inside a radiation area may have the same pixel values. Thus, for example, an area segment outside a radiation area that has pixel values more than a threshold value and an area segment inside the radiation area that has pixel values equal to or less than the threshold value may exist, as shown in FIG. 3. However, since most area segments outside a radiation area that have pixel values more than a threshold value are located around the edges of the radiation area, the corresponding barycenter is likely to be located within the radiation area. Thus, it is highly probable that the calculated barycenter of a predetermined number or more of pixels is located within the radiation area.

Figure 4:
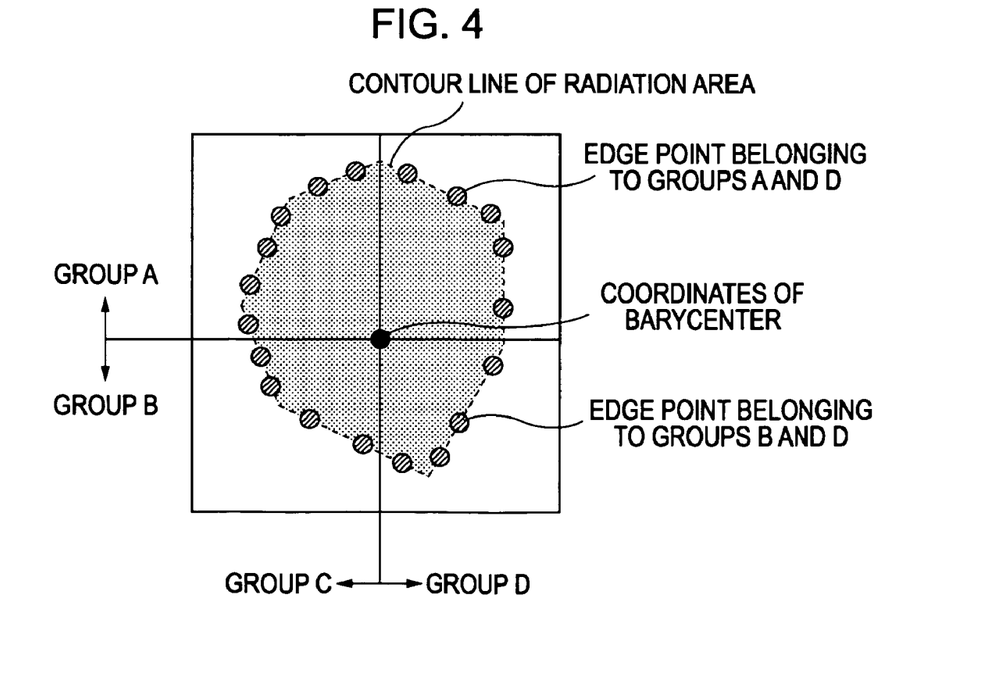
FIG. 4 is used to show a method for classifying an area.

FIG. 4 is used to show a method for classifying the area segments of image data with the obtained barycenter being their center. For example, an area is divided with respect to the barycenter vertically into two area segments corresponding to groups A and B and horizontally into two area segments corresponding to groups C and D, i.e., in total four area segments, and edge points that are located in the individual area segments are classified into edge points that belong to the corresponding groups, as shown in FIG. 4. In this exemplary embodiment, each of the area segments overlaps two other area segments. For example, edge points that are located to the upper right of the barycenter are classified as edge points that belong to two groups (groups A and D). The method for dividing an area is not limited to the aforementioned method. Alternatively, the area may be divided into the area segments so that the area segments do not overlap each other, or the area may be divided into more area segments.

It can be determined by the aforementioned method which line segment out of line segments that constitute the edges of the radiation area an edge point corresponds to. Moreover, in the aforementioned method, the area segments are determined with respect to the barycenter. Thus, even when the radiation area is disposed at any position in the entire image, edge points can be classified in the same manner as described above.

Next, the edge points classified into groups A, B, C, and D are further classified according to the gradient directions of the edge points. The gradient directions θ(x, y) of edge points f(x, y) can be calculated by the following equation (4) and fall into a range of −π/2 to π/2.

$$\theta(x, y) = \arctan\left(\frac{\partial f(x, y)}{\partial y} \bigg/ \frac{\partial f(x, y)}{\partial x}\right) \quad (4)$$

In equation (4), the partial derivative with respect to x or y can be calculated using a derivative operator, such as a generally known Sobel, Prewitt, or Roberts operator.

The edge points in each of the four groups are further classified into subgroups each including edge points oriented in the same direction on the basis of the calculated gradient directions. For example, the edge points that belong to each group are classified into eight subgroups corresponding to directions spaced every π/8. This classification is performed on all of the groups A, B, C, and D to classify all of the edge points into sixty-four subgroups. In this case, the divided area segments may overlap each other. Moreover, when the radiation area has a rectangular shape, the radiation area may be divided at intervals of about π/2. When the radiation area has a polygonal or circular shape, the radiation area should be divided at short intervals.

It is highly probable that the edge points in each of the subgroups, which are classified by the aforementioned method, are located on the same line segment that constitutes the contour line of the radiation area.

Then, in step S204, the line-segment generating circuit 113 generates a plurality of line segments for each subgroup of edge points, which are classified in step S203. The line segments are referred to as candidate lines that are assumed to constitute a contour line that represents the outer edges of the radiation area.

Although candidate lines may be generated in the area of image data without limitation, candidate lines are extracted by, for example, the following method for the sake of reducing the amount of calculation.

The method for generating candidate lines is not limited to a specific method, and candidate lines can be generated by, for example, the Hough transformation.

Line segments that pass through edge points of greater than or equal to a predetermined threshold number can be generated as candidate lines that constitute the edges of the radiation area. The threshold number can be determined on the basis of the statistical data. For example, the threshold number can be statistically determined in advance on the basis of the actual number of edge points through which a line segment that constitutes the correct contour line of a radiation area passes. When the threshold number is set to a small number, a large number of candidate lines that represent the edges of a radiation area may be extracted. In contrast, when the threshold number is set to a large number, the number of candidate lines may decrease. However, correct candidate lines may not be extracted. Thus, the threshold number should be set in a range such that correct candidate lines can be extracted.

When the number of candidate lines that exist in a classified subgroup of edge points is less than the threshold number, the subgroup is regarded as a subgroup that does not include any line segment that constitutes the contour line. In this case, in the area segment corresponding to the subgroup, the edges of the radiation area are supposed to reach the edges of the light receiver. Such a state may be called a state in which the radiation area is out of focus. In this state, radiation reaches the edges of the light receiver in the area segment. In step S205, it is determined whether any of the subgroups include a candidate line. When it is determined that none of the subgroups include a candidate line, the process shown in FIG. 2 is completed. Otherwise, the process proceeds to step S206.

Figure 5:
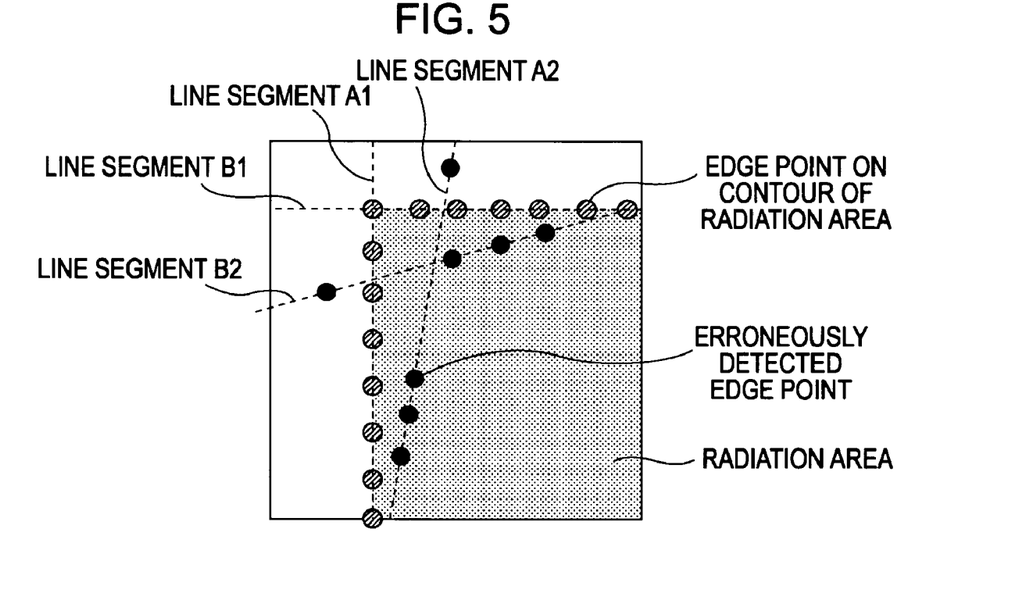
FIGS. 5 and 6 are used to show a method for extracting candidate lines.

FIG. 5 shows example combinations of candidate lines in the subgroups.

Figure 6:
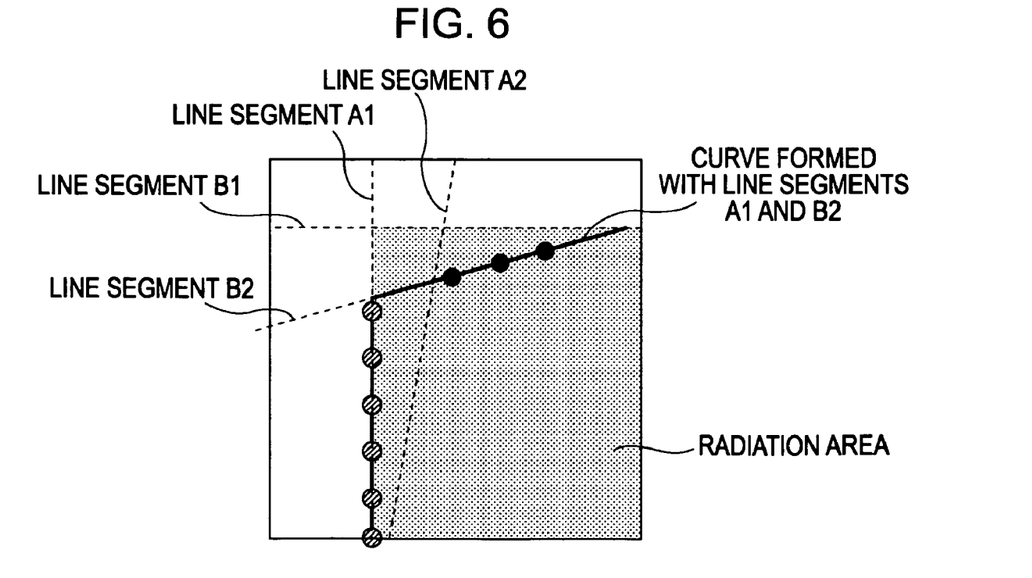

FIG. 6 shows an example of a selected combination of candidate lines.

Two line segments A1 and A2 are generated as candidate lines in a subgroup A, and two line segments B1 and B2 are generated as candidate lines in a subgroup B, as shown in FIG. 5. In this case, selectable combinations are (A1, B1), (A1, B2), (A2, B1), and (A2, B2). In this situation, the evaluating circuit 114 selects candidate lines one by one from each of the subgroups, which are generated by the line-segment generating circuit 113, and generates combinations of candidate lines. Then, the evaluating circuit 114 evaluates the combinations of candidate lines.

In step S206, one or no candidate line is selected from each subgroup. For example, in the case shown in FIG. 5, combinations (A1, B1), (A1, B2), (A2, B1), and (A2, B2) are selected. Moreover, combinations in each of which no line segment is selected from either of the subgroups, excluding a combination in which no line segment is selected from all of the subgroups, can be selected, i.e., (A1, no selection), (no selection, B1), (A2, no selection), and (no selection, B2). Thus, curves are generated with eight combinations in total. In this case, no selection of a line segment means that the radiation area reaches the edges of the light receiver, as shown in the lower right part of FIG. 5. For example, when (A1, B2) is selected in FIG. 5, a curve shown in FIG. 6 is generated. In this exemplary embodiment, a line formed by linking line segments together is called a curve, each line segment being formed between one intersecting point of candidate lines and another intersecting point of candidate lines. In the case shown in FIG. 6, only one intersecting point exists. In such a case, a line formed by linking line segments together is called a curve, each line segment being formed between the only one intersecting point and the edges of the image data, i.e., the edges of the light receiver.

Then, in step S207, curves generated with the selected combinations of candidate lines are evaluated. For example, this evaluation is performed so that the number of edge points located on each curve is the evaluated value of each of the selected combinations of candidate lines. In this evaluation, the characteristic amount of each edge point is one.

For example, when the combination (A1, B2) is selected as shown in FIG. 6, the evaluated value of the corresponding curve is nine. The edge points are extracted in step 201 as edge points that are supposed to be on the contour line of the edges of the radiation area. Thus, the larger the evaluated value, the higher the probability that the corresponding curve includes line segments on the contour line of the radiation area.

The gradient values of the edge points on the contour line of the radiation area are relatively high compared with those of other edge points that are not on the contour line of the radiation area. Thus, the gradient values of the edge points on the corresponding curve may be used as the characteristic amounts, and the total of the characteristic amounts of the curve may be used as the evaluated value of the corresponding selected combination of line segments. This arrangement is preferable because the gradient values of the edge points are incorporated.

Figure 7:
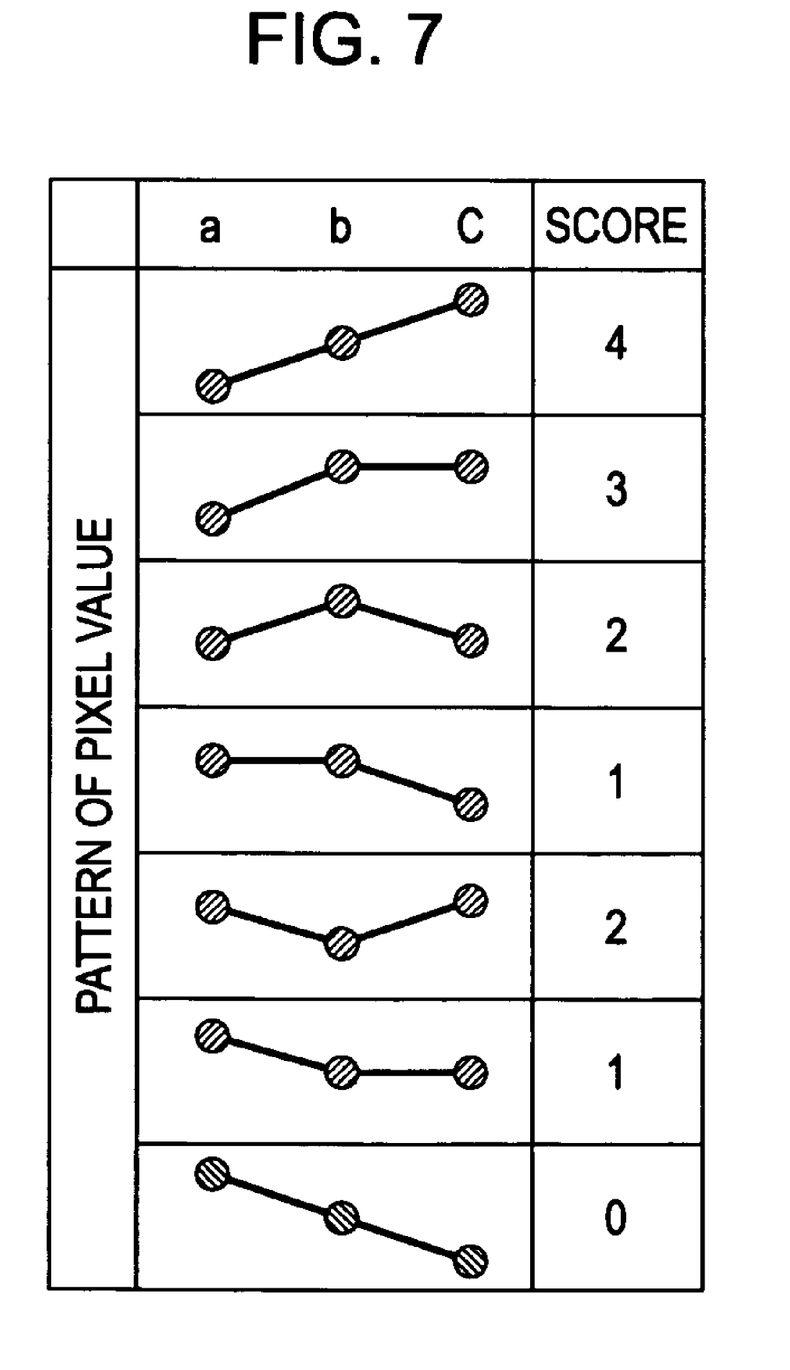
FIG. 7 shows patterns of pixel values.

FIG. 7 is used to describe in detail another case where a pattern of pixel value that represents information related to the gradient of each edge point is used as the characteristic amount. In FIG. 7, reference letter a represents the pixel value of a coordinate point that is distant from the barycenter, reference letter b represents the pixel value of an edge point to be evaluated, and reference letter c represents the pixel value of a coordinate point that is close to the barycenter.

The evaluated value of each edge point that is obtained by evaluating the corresponding pattern of pixel value in the gradient direction can be used as the characteristic amount of the edge point, the evaluated value of the edge point representing a value related to the gradient of the edge point, as described above. Since the edges of the radiation area form the boundary between an area that is shielded from radiation and an area to which radiation is emitted, the pixel value tends to increase in the direction from the outside of the edges of the radiation area to the inside. Thus, a high score is given to this pattern of pixel value, and a low score is given to a pattern of pixel value, in which the pixel value tends to decrease in the aforementioned direction. In this way, a score is given to each edge point as the characteristic amount. In this case, three points are used to determine the pattern of pixel value. However, the method for determining the pattern of pixel value is not limited to this method, and more than three points may be used to determine the pattern of pixel value.

A score can be given to each edge point on the basis of the corresponding pattern of pixel value, as described above, and the total of the characteristic amounts of the edge points located on a curve can be used as the evaluated value of the corresponding selected combination of line segments. A characteristic amount that is obtained by multiplying a score given to each edge point by the gradient value of the edge point may be used to calculate the evaluated value of the corresponding selected combination of line segments. Moreover, an average value may be obtained by dividing the total of the characteristic amounts of edge points by the number of edge points or the length of line segments and may be used as the evaluated value of the corresponding selected combination of line segments. In this case, a statistical value, such as a median value other than an average value, may be used.

Then, in step S208, it is determined whether all of the combinations of candidate lines have been evaluated. When it is determined that all of the combinations of candidate lines have been evaluated, the process proceeds to step S209. Otherwise, the process goes back to S206. In step S209, one combination of candidate lines that is supposed to constitute the contour line of the radiation area is selected from all of the combinations of candidate lines on the basis of the evaluated values obtained by the evaluating circuit 114.

Then, the radiation area is extracted. In this extraction process, an area segment surrounded by the candidate lines that have been selected as line segments that constitute the contour line that represents the outer edges of the radiation area is extracted as the radiation area.

In the aforementioned description, a radiation area formed with two line segments was described in detail. However, even when the radiation area is formed with three or more groups of line segments, the radiation area can be readily extracted by repeating the aforementioned method.

Figure 8:
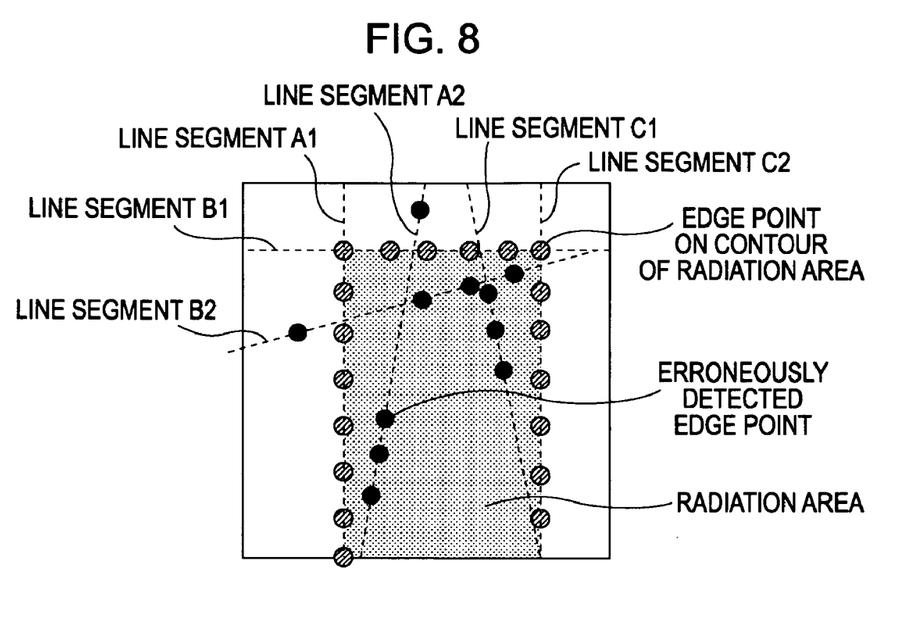
FIGS. 8 and 9 are used to show a method for extracting candidate lines.

FIG. 8 shows a case where two candidate lines are extracted from each of three groups A, B, and C.

Figure 9:
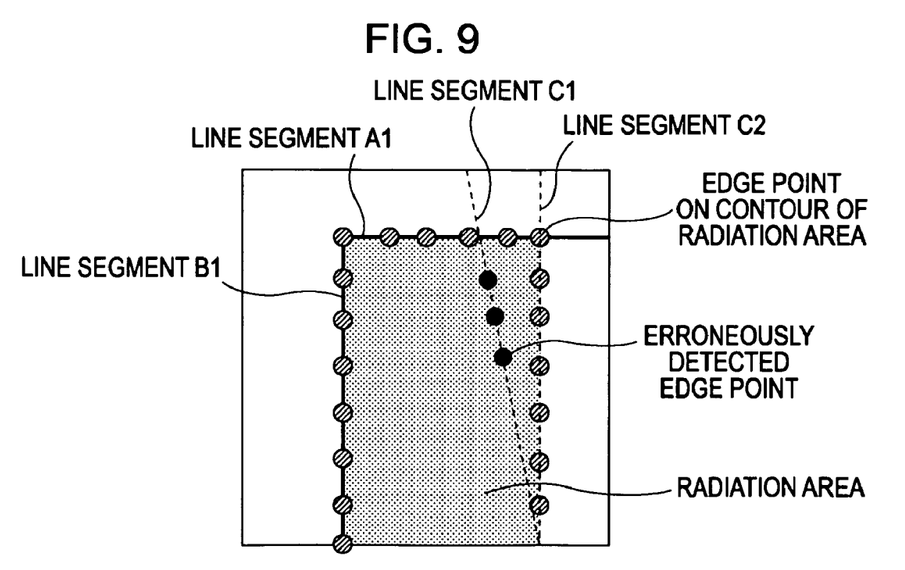

FIG. 9 show a case where a candidate line C2 is selected by evaluating the relationship between the candidate line C2 and a line segment A1 that is a candidate line.

For example, when two line segments are extracted from each of the three groups A, B, and C as candidate lines, as shown in FIG. 8, a first group is selected, and then a second group that includes candidate lines that intersect with candidate lines included in the first group is selected. For example, in FIG. 8, the group A is selected as the first group, and then the group B that includes candidate lines that intersect with candidate lines includes in the group A is selected as the second group. Then, combinations of the line segments included in the groups A and B are evaluated, as described above, and line segments A1 and B1 are selected, as shown in FIG. 9.

Figure 10:
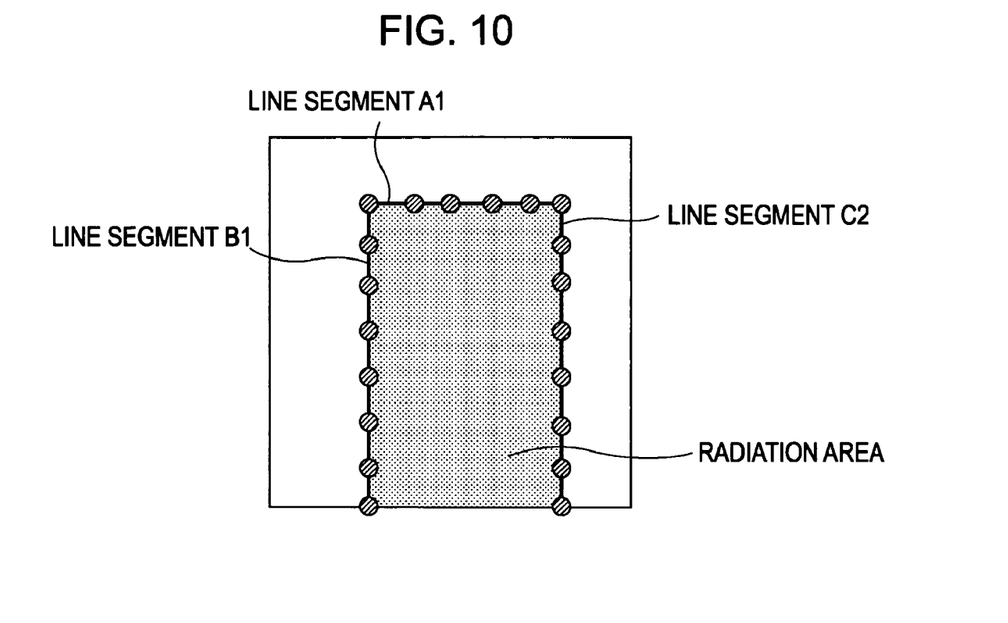
FIG. 10 shows the exemplary result of extracting a radiation area.

Then, a third group that includes candidate lines that intersect with a curve that is formed with the selected candidate lines A1 and B1 is selected. For example, in FIG. 9, the group C is selected as the third group. Then, combinations of the line segments A1 and B1 and the line segments included in the group C are evaluated as described above, and a candidate line C2 is selected. Finally, it is determined that the contour line of the radiation area is a curve that includes the candidate lines A1, B1, and C2, as shown in FIG. 10.

In the aforementioned description, the case where the radiation area is formed with three groups of line segments was described. However, even when the radiation area is formed with four or more groups of line segments, the radiation area can be extracted by the aforementioned method. That is to say, even when the radiation area has a rectangular or polygonal shape, the radiation area can be extracted as described above.

When line segments that constitute the edges of a radiation area are extracted, the relationship between one candidate line and another candidate line is evaluated, as described above. Thus, an advantage can be achieved in that the frequency with which the radiation area is erroneously extracted is decreased. In particular, a large number of edge points are located on line segments that constitute the edges of a radiation area. Thus, it is highly probable that a combination of candidate lines that pass through a large number of edge points is a combination of line segments that constitute the edges of the radiation area.

Second Exemplary Embodiment

A second exemplary embodiment is different from the first exemplary embodiment in the method for evaluation that is performed by the evaluating circuit 114 in the radiography apparatus 100 shown in FIG. 1. The same reference numerals as in the first exemplary embodiment are assigned to the corresponding components, and the description of these components is omitted.

The evaluating circuit 114 evaluates combinations of candidate lines that are selected from individual groups that are extracted by the line-segment generating circuit 113. In the second exemplary embodiment, evaluation is performed on the basis of the crossing angle between two candidate lines. For example, when radiation is emitted from a rectangular emitting aperture, the radiation area has a substantially rectangular shape. Thus, the vertex angle of the contour line of the radiation area is substantially ninety degrees. That is to say, in a case where the radiation area has a rectangular shape, it is highly probable that a combination of candidate lines that intersect with each other at an angle close ninety degrees is a correct combination of candidate lines. Thus, when evaluation is performed so that the evaluated value of a combination of candidate lines that intersect with each other at an angle close ninety degrees is high, a correct combination of candidate lines that constitute a rectangular radiation area can be selected.

Figure 11:
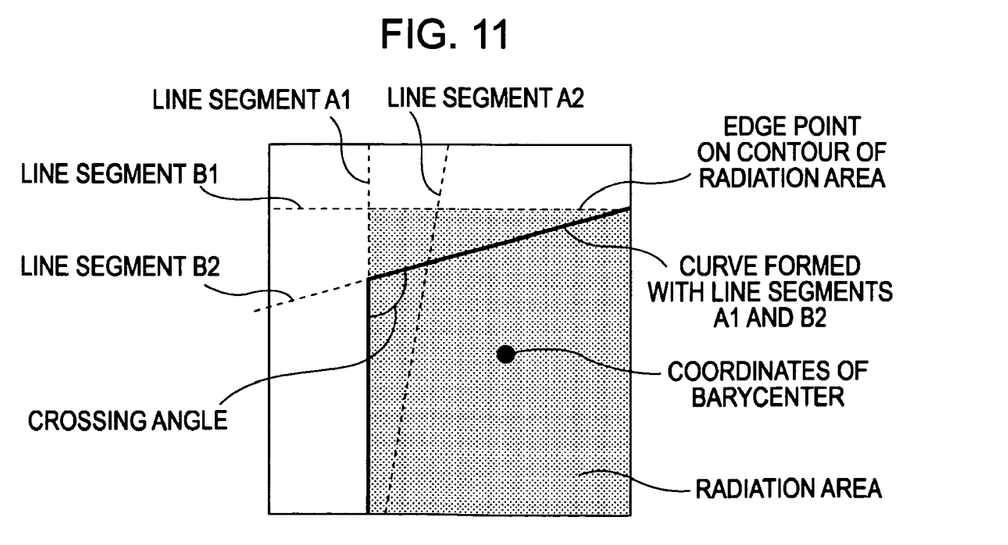
FIG. 11 is used to show a method for extracting candidate lines.

FIG. 11 shows a case where a combination of candidate lines that represent the edges of a radiation area is selected from line segments A1, A2, B1, and B2 that are candidate lines.

For example, when the line segments A1 and B1 are selected as the candidate lines, the crossing angle θ between these line segments on the barycenter side is calculated. The evaluated value S of a selected combination of candidate lines is calculated by the following equation (6) with a predetermined reference crossing angle $\theta_0$.

$$S = 1 - (|\theta - \theta_0|/180) \quad (6)$$

According to equation (6), the evaluated value S takes on the maximum value one when the difference between the predetermined reference crossing angle $\theta_0$ and the crossing angle θ is minimum and decreases as the difference increases. When the radiation area has a rectangular shape, the predetermined reference crossing angle $\theta_0$ is set to ninety degrees. Then, when the crossing angle θ is ninety degrees, the evaluated value S takes on the maximum value one. When the radiation area has a polygonal shape, evaluation can be performed by setting the predetermined reference crossing angle $\theta_0$ to a value corresponding to the shape of the radiation area.

The method for evaluation is not limited to the method defined by equation (6), and another method for evaluation based on the crossing angle between line segments can be used.

In the second exemplary embodiment, the relationship between candidate lines is evaluated on the basis of the crossing angle between the candidate lines. The shape of a radiation area is determined by the shape of an emitting aperture. Thus, when the crossing angle between candidate lines is taken into consideration, the accuracy of extracting a radiation area can be improved. When an emitting aperture has a polygonal shape other than a rectangular shape, evaluation can be performed with a predetermined reference crossing angle $\theta_0$ corresponding to the polygonal shape. In this case, equation (6) is transformed.

Third Exemplary Embodiment

A third exemplary embodiment is different from the first exemplary embodiment in the method for evaluation that is performed by the evaluating circuit 114 in the radiography apparatus 100 shown in FIG. 1. The same reference numerals as in the first exemplary embodiment are assigned to the corresponding components, and the description of these components is omitted.

The evaluating circuit 114 evaluates combinations of candidate lines that are selected from individual groups that are extracted by the line-segment generating circuit 113. In the third exemplary embodiment, evaluation is performed on the basis of the characteristic amounts of edge points and the crossing angle between two candidate lines. In the third exemplary embodiment, the method for evaluation based on the characteristic amounts of edge points is the same as that according to the first exemplary embodiment, the method for evaluation based on the crossing angle between two candidate lines is the same as that according to the second exemplary embodiment, and a value that is obtained by multiplying the values obtained by these two methods together is used as the evaluated value of a selected combination of candidate lines. Alternatively, a value that is obtained by normalizing and adding the values obtained by these two methods may be used as the evaluated value of a selected combination of candidate lines.

In the third exemplary embodiment, the method for evaluation based on the characteristic amounts of edge points and the method for evaluation based on the crossing angle between two candidate lines are used in combination as the methods for evaluating the relationship between candidate lines. Thus, two different criteria for evaluation are used, and a radiation area can be accurately extracted.

Fourth Exemplary Embodiment

A fourth exemplary embodiment is different from the first exemplary embodiment in the method for evaluation that is performed by the evaluating circuit 114 in the radiography apparatus 100 shown in FIG. 1. The same reference numerals as in the first exemplary embodiment are assigned to the corresponding components, and the description of these components is omitted.

The evaluating circuit 114 evaluates combinations of candidate lines that are selected from individual groups that are extracted by the line-segment generating circuit 113. In the first exemplary embodiment, for example, when three or more groups exist, candidate lines are sequentially selected from the individual groups.

The fourth exemplary embodiment is different from the first exemplary embodiment in that candidate lines are selected at the same time.

Figure 12:
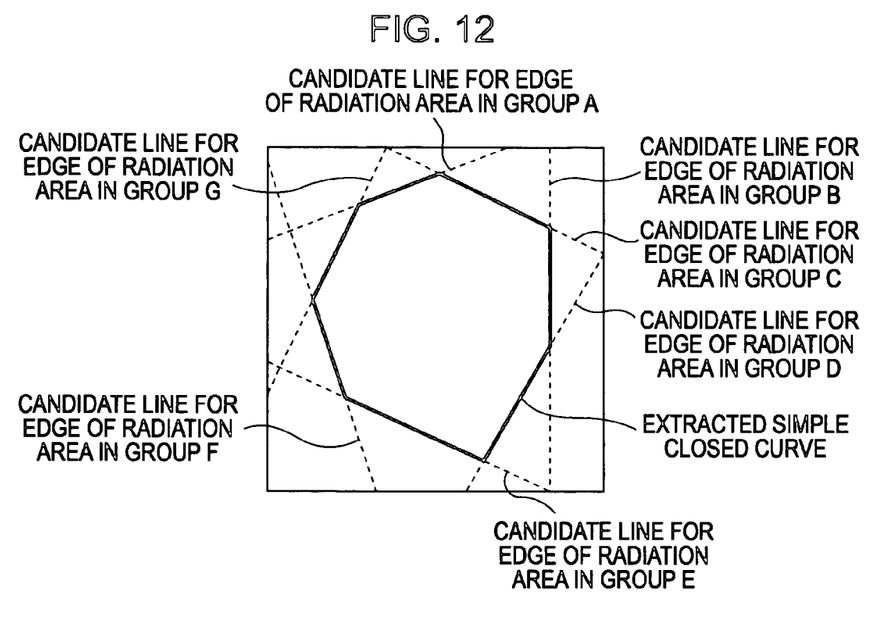
FIG. 12 shows the exemplary result of extracting a closed curve.
Figure 13:
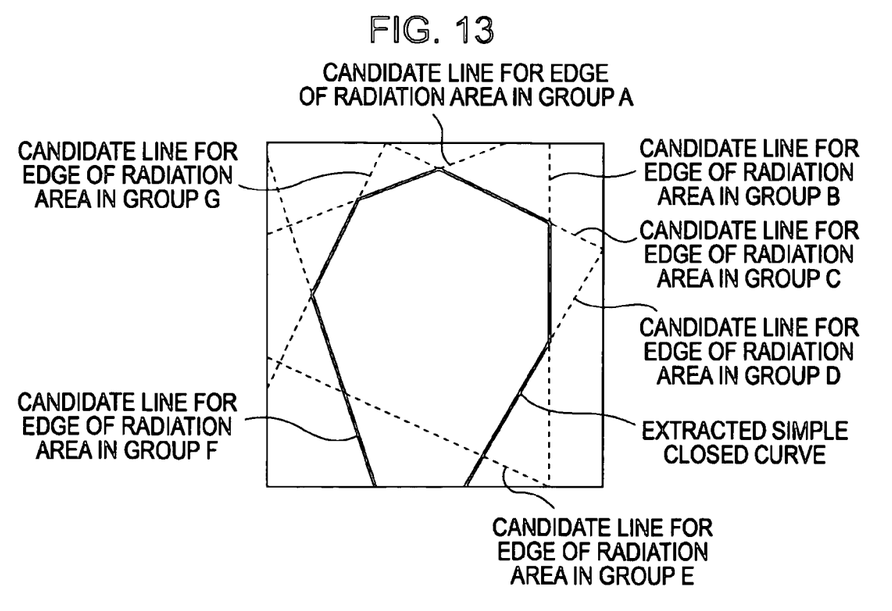
FIG. 13 shows the exemplary result of extracting a closed curve that includes an edge of an image as a candidate line.
Figure 14:
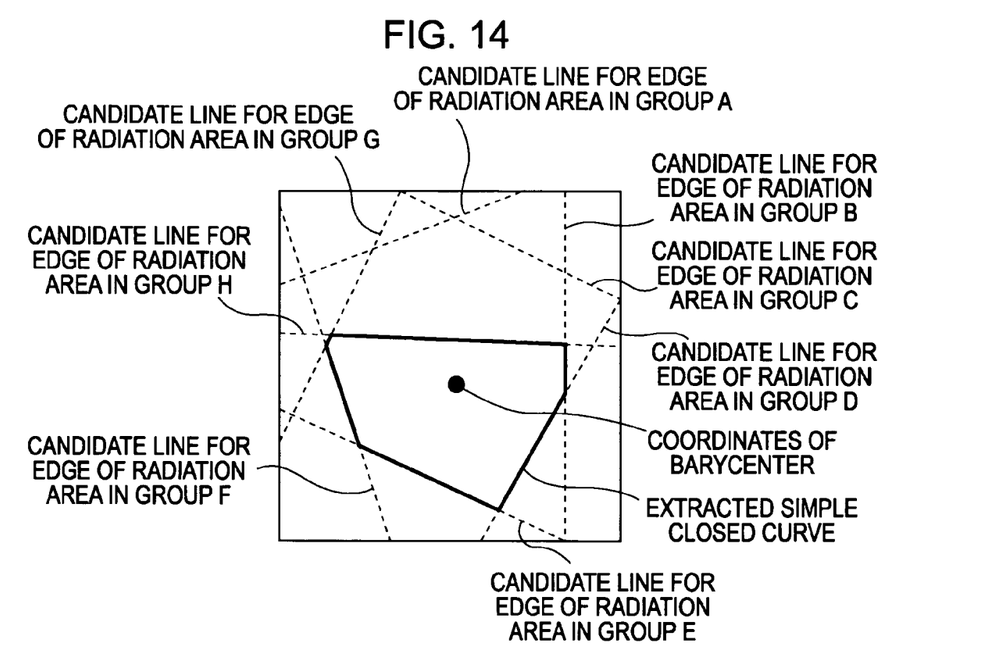
FIG. 14 shows the exemplary result of extracting a closed curve.

FIGS. 12, 13, and 14 show cases where candidate lines are selected from a plurality of groups.

A candidate line that is supposed to constitute the edges of a radiation area is first selected from each group. For example, when four groups A, B, C, and D each include two candidate lines, either of the two candidate lines is selected from each group. Moreover, no candidate line may be selected from the group A, and one candidate line may be selected from each of the groups B, C, and D. However, a case where no candidate line is selected from all of the groups is excluded. Thus, when the four groups A, B, C, and D each include two candidate lines, one combination is sequentially selected from eleven combinations of candidate lines.

Then, a line enclosed with the candidate lines included in the selected combination is extracted as a simple closed curve of the selected combination. That is to say, the extracted line is formed with line segments, each line segment being formed between one intersecting point of candidate lines and another intersecting point of candidate lines. For example, a simple closed curve formed with candidate lines that are selected from individual seven groups A to G is shown in FIG. 12. When no candidate line is selected from the group E, a line enclosed with line segments including a line segment that represents an edge of an image and that is treated as a candidate line is extracted as a simple closed curve, as shown in FIG. 13. Moreover, when a plurality of simple closed curves that are formed with candidate lines that are selected from groups A to H exist, as shown in FIG. 14, one simple closed curve that includes the barycenter and has the smallest area is extracted.

In this way, simple closed curves are generated with all of the combinations of candidate lines.

Then, the evaluating circuit 114 calculates the total of characteristic amounts of edge points on each simple closed curve that is formed with the corresponding combination of candidate lines.

Then, the line-segment extracting circuit 115 finally selects a simple closed curve that has the largest total of characteristic amounts as a simple closed curve that constitutes a contour line that represents the outer edges of the radiation area. The edge points are extracted as points that are strongly supposed to be located on the edges of the radiation area, as described above. Thus, it is highly probable that a simple closed curve that has the largest total of characteristic amounts constitutes the edges of the radiation area.

Figure 15:
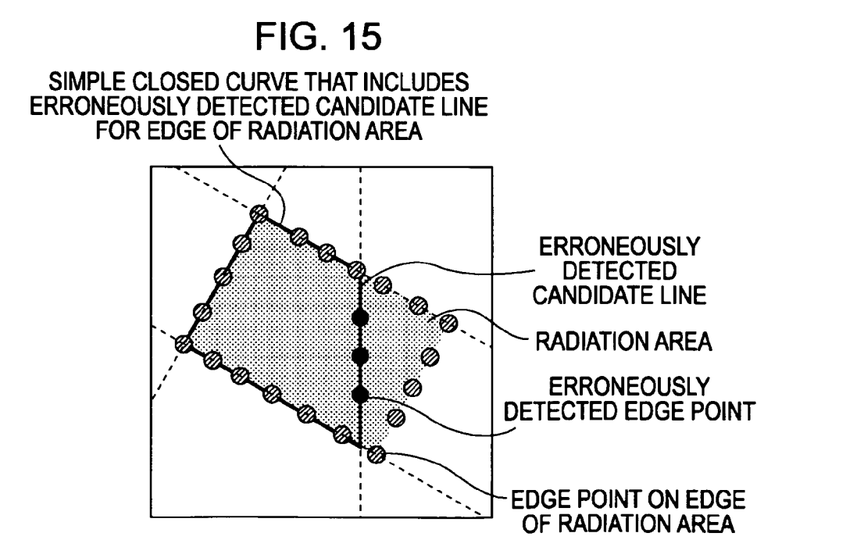
FIG. 15 shows an exemplary closed curve that includes an erroneously detected candidate line.

FIG. 15 shows a case where edge points of, for example, a lipping or a piece of metal exist in a radiation area.

Figure 16:
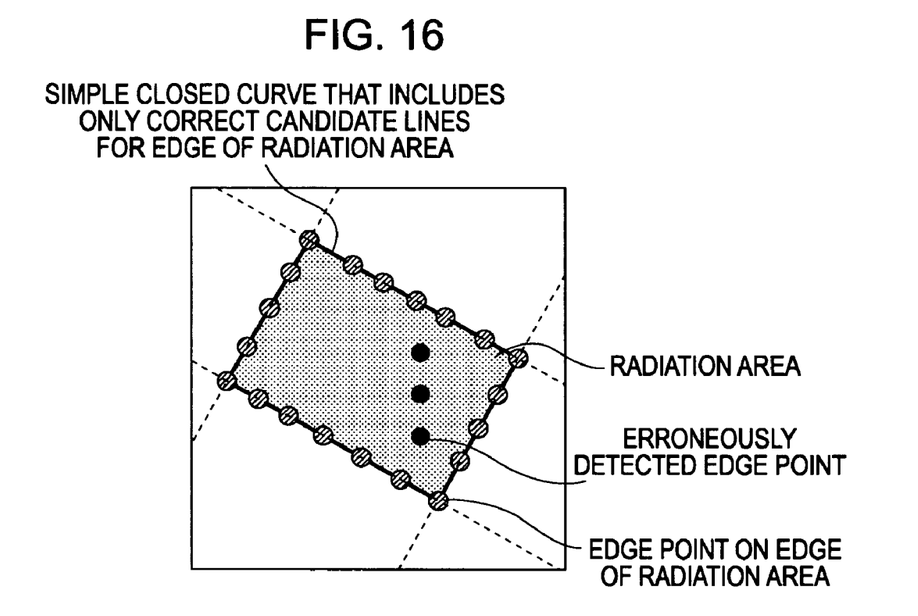
FIG. 16 shows the exemplary result of extracting a correct closed curve.

FIG. 16 shows a radiation area that is formed with correct candidate lines that are supposed to constitute the edges of the radiation area.

In the fourth exemplary embodiment, even when a candidate line that is erroneously extracted from, for example, a lipping or a piece of metal that has a straight part exists, the edges of the radiation area can be correctly determined. This is because edge points of a lipping or a piece of metal exist in the radiation area and a simple closed curve that includes an erroneously extracted candidate line breaks the outer edges of a correct radiation area, as shown in FIG. 15. Thus, such a simple closed curve that includes an erroneously extracted candidate line is not selected as a simple closed curve that constitutes the outer edges of the radiation area on the basis of the criteria for evaluation. That is to say, even when a candidate line is erroneously detected, a simple closed curve that is formed with a combination of correct candidate lines passes through the most edge points, as shown in FIG. 16. Thus, it is determined that such a simple closed curve is a simple closed curve that constitutes the outer edges of the radiation area.

In the fourth exemplary embodiment, when a plurality of groups exist, candidate lines are selected at the same time. Thus, all of the candidate lines can be evaluated at the same time, and a radiation area can be accurately extracted.

Fifth Exemplary Embodiment

A fifth exemplary embodiment is different from the fourth exemplary embodiment in that the area extracting circuit 116 in the radiography apparatus 100 shown in FIG. 1 has a verification function. The same reference numerals as in the fourth exemplary embodiment are assigned to the corresponding components, and the description of these components is omitted.

In the fifth exemplary embodiment, an average value of characteristic amounts of edge points that are located on a determined candidate line is calculated by dividing the total of the characteristic amounts of the edge points by the number of the edge points.

Then, it is determined by comparing the average value of the characteristic amounts with a predetermined threshold value whether the finally selected candidate line constitutes the outer edges of a radiation area. When the outer edges of the radiation area reach the edges of the light receiver, the data of the outer edges of the radiation area may not exist in the image data. In view of such a condition, when the average value of the characteristic amounts is equal to or less than the predetermined threshold value, it is determined that the candidate line does not constitute the outer edges of the radiation area. Such a state in which the outer edges of the radiation area reach the edges of the light receiver is called a state in which the radiation area is out of focus. In this state, it is determined that any outer edge of the radiation area does not exist in the area segment from which the candidate line, which is judged not to be the outer edges of the radiation area, is extracted. Thus, the edge of the image in such an area segment is newly selected as a part of the outer edges of the radiation area (for example, the group E in FIG. 13). In the fifth exemplary embodiment, it is determined on the basis of the average value of the characteristic amounts whether the radiation area is out of focus, as described above. In this arrangement, it can be determined regardless of the lengths of the edges of the radiation area (the size of the radiation area) whether the radiation area is out of focus. In a case where the radiation area is extremely narrowed down (a case where the size of the radiation area is small), the number of edge points on the corresponding simple closed curve decreases, and thus the total of the characteristic amounts of the edge points decreases. In contrast, the average value of the characteristic amounts of the edge points does not depend on the number of the edge points. Thus, a stable evaluated value can be calculated regardless of the size of the radiation area, and the aforementioned advantage can be achieved.

In the fifth exemplary embodiment, an average value is used. However, even when a statistical value, such as a median value, is used as the criteria for evaluation, the same advantage can be achieved.

In the fifth exemplary embodiment, the average value of characteristic amounts of edge points is used. Thus, even when a radiation area is extremely narrowed down, the radiation area can be accurately extracted.

Sixth Exemplary Embodiment

A sixth exemplary embodiment is different from the fourth exemplary embodiment in that the area extracting circuit 116 in the radiography apparatus 100 shown in FIG. 1 has a verification function. The same reference numerals as in the fourth exemplary embodiment are assigned to the corresponding components, and the description of these components is omitted.

Figure 17:
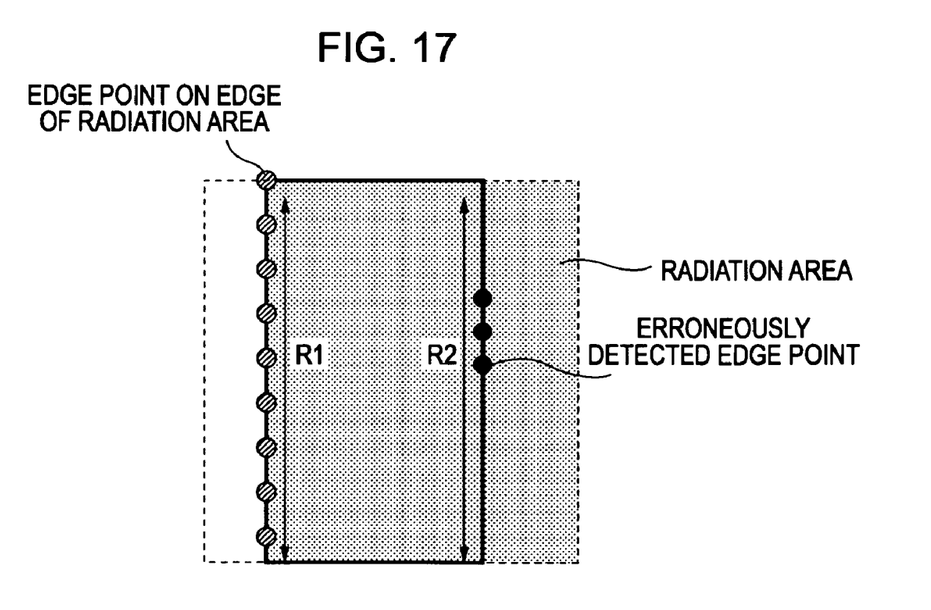
FIG. 17 shows a case where extracted candidate lines are parallel to each other.

FIG. 17 shows an example of a radiation area in which a simple closed curve includes two candidate lines that do not intersect with each other.

The area extracting circuit 116 first determines whether candidate lines that are finally selected include candidate lines that are parallel to each other. When the area extracting circuit 116 determines that the candidate lines include candidate lines that are parallel to each other, a candidate line that is supposed to constitute the edges of the radiation area is erroneously detected in some cases, as shown in FIG. 17. This is because edge points exist only on candidate lines R1 and R2 and the total of the characteristic amounts of the edge points located on a simple closed curve that includes the erroneously detected candidate line is largest.

In many cases, a line segment that represents the outer edge of a correct radiation area includes a long straight part that connects the upper and lower edges of the sensor, as shown in FIG. 17. In contrast, a lipping, a piece of metal, or the like in the subject includes a short straight part. That is to say, the ratio of the total of the characteristic amounts of the edge points on the erroneously detected candidate line to the length of the erroneously detected candidate line is small. Thus, a value is obtained as density of each candidate line by dividing the total of the characteristic amounts of edge points on each candidate line (in FIG. 17, each of the candidate lines R1 and R2) by the length of each candidate line. The density of the candidate line that represents the outer edge of a correct radiation area is large because the candidate line includes a long straight part. In contrast, the density of the erroneously detected candidate line is small. Accordingly, when the density of a candidate line is equal to or less than a predetermined threshold value, it is determined that the candidate line is an erroneously detected candidate line. Thus, the candidate line is excluded, and the corresponding simple closed curve is restructured with candidate lines other than the excluded candidate line. That is to say, in the case shown in FIG. 17, when the densities of both of the two candidate lines exceed the threshold value, it is determined that the corresponding simple closed curve is a correct simple closed curve that is formed with the two candidate lines. When the density of either of the two candidate lines is equal to or less than the threshold value, the corresponding simple closed curve is restructured with one candidate line. When the densities of both of the two candidate lines are equal to or less than the threshold value, it is determined that the radiation area is out of focus.

In the sixth exemplary embodiment, the aforementioned criteria for evaluation are added. Thus, even a radiation area that is formed with two or less parallel candidate lines can be accurately extracted.

In the aforementioned exemplary embodiments, the image data is obtained through the two-dimensional radiation sensor. The method for obtaining image data is not limited to this method, and, for example, the following methods can be used. In another method, radiation is received through a light receiver and is stored on a stimulable phosphor sheet. Then, the stimulable phosphor sheet is illuminated with excitation light, and photostimulated luminescence from the stimulable phosphor sheet that is caused by this operation is photoelectrically detected to obtain image data to produce a visible image. In yet another method, an analog film that has received radiation through a light receiver included in a cassette case is developed, and the image formed on the developed film is converted to image data by an AD conversion apparatus.

Moreover, the present invention is not limited to a technique in which radiation is used and is also applicable to a technique for extracting a captured image area, the technique being used in, for example, a digital camera that includes a unit that receives light beams in a case where the captured image area is restricted (corresponding to radiation focusing).

The present invention provides a radiation area extracting method and an image capturing apparatus to reduce the frequency with which a radiation area is erroneously extracted, as described above.

Note that the present invention can be applied to an apparatus comprising a single device or to system constituted by a plurality of devices.

Furthermore, the invention can be implemented by supplying a software program, which implements the functions of the foregoing embodiments, directly or indirectly to a system or apparatus, reading the supplied program code with a computer of the system or apparatus, and then executing the program code. In this case, so long as the system or apparatus has the functions of the program, the mode of implementation need not rely upon a program.

Accordingly, since the functions of the present invention are implemented by computer, the program code installed in the computer also implements the present invention. In other words, the claims of the present invention also cover a computer program for the purpose of implementing the functions of the present invention.

In this case, so long as the system or apparatus has the functions of the program, the program may be executed in any form, such as an object code, a program executed by an interpreter, or scrip data supplied to an operating system.

Example of storage media that can be used for supplying the program are a floppy disk, a hard disk, an optical disk, a magneto-optical disk, a CD-ROM, a CD-R, a CD-RW, a magnetic tape, a non-volatile type memory card, a ROM, and a DVD (DVD-ROM and a DVD-R).

As for the method of supplying the program, a client computer can be connected to a website on the Internet using a browser of the client computer, and the computer program of the present invention or an automatically-installable compressed file of the program can be downloaded to a recording medium such as a hard disk. Further, the program of the present invention can be supplied by dividing the program code constituting the program into a plurality of files and downloading the files from different websites. In other words, a WWW (World Wide Web) server that downloads, to multiple users, the program files that implement the functions of the present invention by computer is also covered by the claims of the present invention.

It is also possible to encrypt and store the program of the present invention on a storage medium such as a CD-ROM, distribute the storage medium to users, allow users who meet certain requirements to download decryption key information from a website via the Internet, and allow these users to decrypt the encrypted program by using the key information, whereby the program is installed in the user computer.

Besides the cases where the aforementioned functions according to the embodiments are implemented by executing the read program by computer, an operating system or the like running on the computer may perform all or a part of the actual processing so that the functions of the foregoing embodiments can be implemented by this processing.

Furthermore, after the program read from the storage medium is written to a function expansion board inserted into the computer or to a memory provided in a function expansion unit connected to the computer, a CPU or the like mounted on the function expansion board or function expansion unit performs all or a part of the actual processing so that the functions of the foregoing embodiments can be implemented by this processing.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the priority of Japanese Application No. 2005-159111 filed May 31, 2005, which is hereby incorporated by reference herein in its entirety.

What is claimed is:

1. A radiation area extracting method for extracting a radiation area from image data, the method comprising:
   generating combinations of at least two candidate lines from an area of the image data, each combination of the at least two candidate lines forming a curve having a plurality of edge points;
   an evaluating step of obtaining evaluated values of the combinations of at least two candidate lines based upon a quantity of edge points on the curve for each combination; and
   an extracting step of extracting one of the combinations of at least two candidate lines as a contour line of the radiation area on the basis of the evaluated values,
   wherein the method is performed by a processor.

2. The method according to claim 1, wherein an area that is surrounded by the candidate lines extracted as the contour line is extracted as the radiation area.

3. The method according to claim 1, wherein, in the evaluating step, each evaluated value is obtained by evaluating an angle between the corresponding candidate lines.

4. The method according to claim 3, wherein each evaluated value increases as the angle between the corresponding candidate lines approaches ninety degrees.

5. The method according to claim 1, wherein the evaluating step includes:
   a calculating step of calculating gradients of the image data as characteristic amounts; and
   an adding step of adding the characteristic amounts of each combination of candidate lines to obtain a total for each combination of candidate lines, wherein each evaluated value is the total for each combination of candidate lines.

6. The method according to claim 1, wherein the evaluating step includes:
   a first calculating step of evaluating an angle between the corresponding candidate lines to obtain a first evaluated value;
   a second calculating step of calculating gradients of the image data as characteristic amounts; and
   an adding step of adding the characteristic amounts of each combination of candidate lines to obtain a total for each combination of candidate lines as a second evaluated value, wherein each evaluated value of the corresponding combination of candidate lines is obtained on the basis of the first and second evaluated values.

7. The method according to claim 1, wherein the generating step includes:
- a calculating step of calculating gradients of the image data as characteristic amounts;
- a classifying step of classifying the characteristic amounts into groups on the basis of the gradients of the image data represented by the characteristic amounts; and
- an extracting step of extracting candidate lines for each group.

8. The method according to claim 7, wherein the classifying step includes:
- classifying the area of the image data into a plurality of area segments; and
- classifying the characteristic amounts for each area segment into groups on the basis of the gradients of the image data represented by the characteristic amounts.

9. A computer-readable medium having recorded thereon a radiation area extracting program for extracting a radiation area from image data, which when loaded into a computer and executed performs a method comprising:
- generating combinations of at least two candidate lines from an area of the image data, each combination of the at least two candidate lines forming a curve having a plurality of edge points;
- an evaluating step of obtaining evaluated values of the combinations of at least two candidate lines based upon a quantity of edge points on the curve for each combination; and
- an extracting step of extracting one of the combinations of at least two candidate lines as a contour line of the radiation area on the basis of the evaluated values.

10. An image processing apparatus comprising:
- an image capturing unit that converts radiation that is received through a light receiver to image data;
- a line-segment generating circuit that generates combinations of at least two candidate lines from an area of the image data, each combination of the at least two candidate lines forming a curve having a plurality of edge points;
- an evaluating circuit that obtains evaluated values of the combinations of at least two candidate lines based upon a quantity of edge points on the curve for each combination; and
- a line-segment extracting circuit that extracts one of the combinations of at least two candidate lines as a contour line of the radiation area on the basis of the evaluated values.

* * * * *